Figure 1:
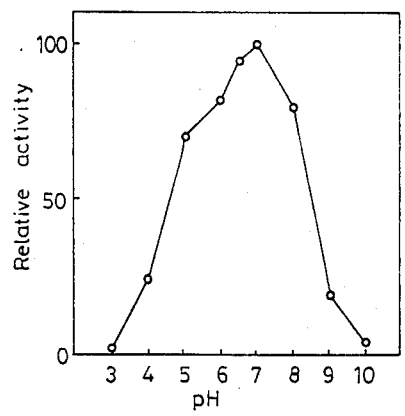

United States Patent [19]

Matsui et al.

[11] Patent Number: 4,610,963

[45] Date of Patent: Sep. 9, 1986

[54] NOVEL GLUTATHIONE OXIDASE, ITS PRODUCTION AND USE

[75] Inventors: Susumu Matsui, Ootsu; Satoko Uchida, Uji; Tsutomu Taniguchi, Kyoto, all of Japan

[73] Assignee: Takara Suzo Co., Ltd., Kyoto, Japan

[21] Appl. No.: 678,767

[22] Filed: Dec. 5, 1984

[30] Foreign Application Priority Data

Dec. 23, 1983 [JP] Japan .................................. 58-250400
Apr. 18, 1984 [JP] Japan .................................. 59-78127

[51] Int. Cl.$^4$ .......................... C12N 9/02; C12Q 1/26; C12R 1/645
[52] U.S. Cl. ...................................... 435/189; 435/25; 435/911
[58] Field of Search ................................ 435/189, 191

[56] References Cited

FOREIGN PATENT DOCUMENTS 57-132879  8/1982  Japan .................................. 435/189
57-146598  9/1982  Japan .

OTHER PUBLICATIONS

Kusakabe et al., Agri. Biol. Chem., vol. 46(8), 2057–2067 (1982).

*Primary Examiner*—Lionel M. Shapiro
*Attorney, Agent, or Firm*—Wenderoth, Lind & Ponack

[57] ABSTRACT

A novel glutathione oxidase which acts on reduced glutathione alone and not no other sulfhydryl compounds is obtained by culturing Calodon or Cortinarius of the class Basidiomycetes.

7 Claims, 7 Drawing Figures

NOVEL GLUTATHIONE OXIDASE, ITS PRODUCTION AND USE

The present invention relates to a novel glutathione oxidase produced by a strain belonging to the genus Calodon or Cortinarius of the class Basidiomycetes and its production, a reagent composition containing said novel glutathione oxidase, a method for the quantitative determination of reduced glutathione (hereinafter referred to as GSH) in test solutions such as biological fluids and foods with said reagent composition, and a method for applying said reagent composition to analytical methods in which the interfering effect of reduced glutathione needs to be eliminated.

GSH is a simple tripeptide having a structure of γ-L-glutamyl-L-cysteinylglycine, and it ranges widely in animals, plants and microorganisms. GSH in living bodies is useful as one component of the amino acid-transporting system, is an activator for some kinds of enzymes as well as a protective agent for preventing the autooxidation of lipids, and besides has an action to detoxicate various deleterious substances. For the measurement of GSH having such important physiological actions, there are so far known chemical methods using reagents such as 5,5'-dithiobis-(2-nitrobenzoic acid), o-phthalaldehyde, etc. which will react with a SH group, and methods using enzymes such as glutathione reductase, glyoxalase I, etc. The former methods are described in Arch. Biochem. and Biophys., Vol. 82, pp. 70 (1959) and Anal. Biochem., Vol. 74, pp. 214 (1976), and the latter ones in J. Biol. Chem., Vol. 227, pp. 339 (1957) and ibid., Vol. 190, pp. 685 (1951). It is however pointed out that these methods have many problems in terms of specificity of reaction and sensitivity as well as complexity of operation, effect of contaminants and the like. In recent years, a method for the quantitative determination of GSH using glutathione sulfhydryl oxidase is reported in Japanese Patent Application Kokai (Laid-open) No. 146598/1982. Since, however, glutathione sulfhydryl oxidase used in this determination acts on not only GSH but also other SH compounds such as L-cysteine, dithiothreitol, etc., this method may not be said to be one having a high specificity toward GSH. Consequently, development of a method has been demanded in which the quantitative determination of GSH in biological fluids (e.g. blood serum, urine) and foods can be attained with enzyme having specificity toward GSH alone.

While a method utilizing oxidase-peroxidase-hydrogen-donative chromogen reaction is recently in wide spread to analyze various components in biological fluids such as blood, urine, etc. and foods. For example, in the measurement of glucose or total cholesterol in blood serum, a colorimetric method in which glucose oxidase or cholesterol esterase or oxidase is made to act on blood serum and the formed hydrogen peroxide is caught with peroxidase, is most popularly employed as a routine inspection method. Particularly, a color-development method with 4-aminoantipyrine-phenol has come to be a leading part of the enzymatic method, in terms of its simplicity and rapidity as well as stability of the reagent. This colorimetric method includes measurement of the formed red quinone dye at 500 nm, but this method has a defect that, since GSH, a reducing substance, in blood serum acts as an hydrogen donor, it interferes with the peroxidase-hydrogen donor color-development system which forms a hydrogen peroxide detection system.

The present inventors made a screening test on glutathione oxidase produced by strains belonging to the class Basidiomycetes, and as a result, found that *Calodon suaveolens* and *Cortinarius bovinus* specifically act on GSH alone in the filtrate of cultured broth to produce glutathione oxidase having excellent properties. The present inventors made a further detailed study on the enzymological properties of this enzyme, and as a result, came to the conclusion that the enzyme of the present invention is glutathione oxidase (hereinafter referred to as novel glutathione oxidase T-1) different from those which are already reported.

Briefly, the present invention relates to the novel glutathione oxidase T-1, and also to a reagent composition for reduced glutathione containing said enzyme.

Also, the present invention relates to a method how to use the novel glutathione oxidase T-1. In one respect of said method, the present invention provides a method for the quantitative determination of GSH which comprises causing a reagent composition containing the novel glutathione oxidase T-1 to act on a GSH-containing test solution and measuring the amount of consumed oxygen or formed hydrogen peroxide in the reaction solution.

In another respect of said method, the present invention provides the following analytical method: In a method for analyzing components other than GSH in a GSH-containing test solution by utilizing the oxidase-peroxidase-hydrogen-donative chromogen reaction in which method GSH acts as an interfering agent, an analytical method characterized in that said method includes (a) a step of causing the reagent composition containing the novel glutathione oxidase T-1 to act on the test solution to eliminate the interfering effect of coexisting GSH and (b) a step of analyzing the desired component present in the remaining test solution.

Further, the present invention provides a method for producing the novel glutathione oxidase T-1 characterized by culturing the said enzyme producing strain belonging to the genus Calodon or Cortinarius and collecting said enzyme from the cultured broth.

Figure 2:
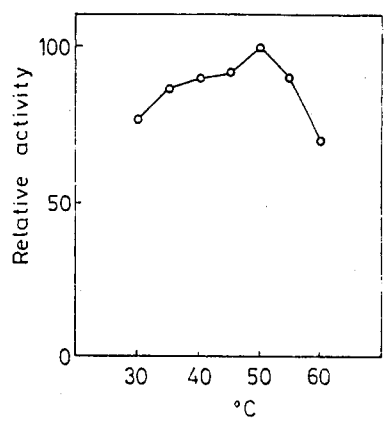
Figure 3:
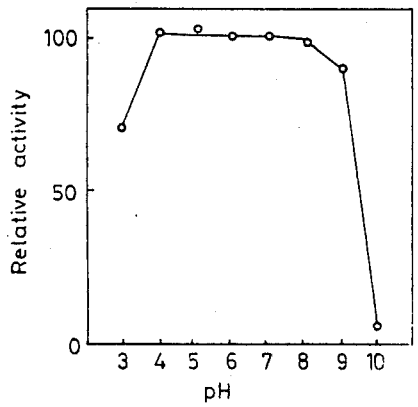
Figure 4:
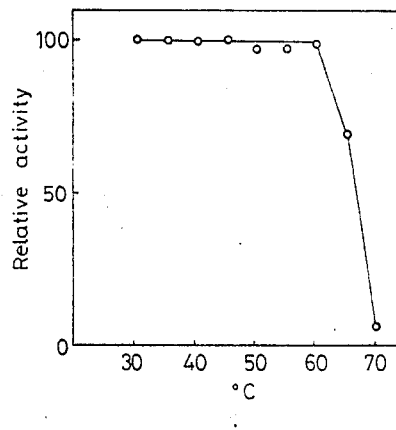
Figure 5:
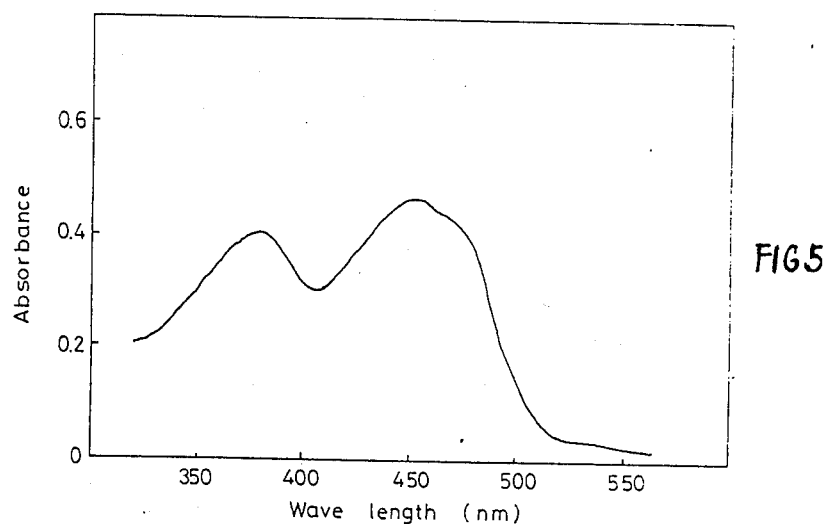
Figure 6:
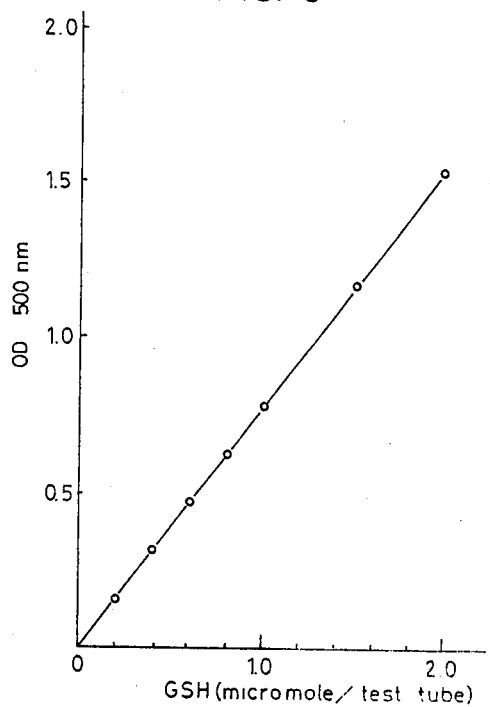
Figure 7:
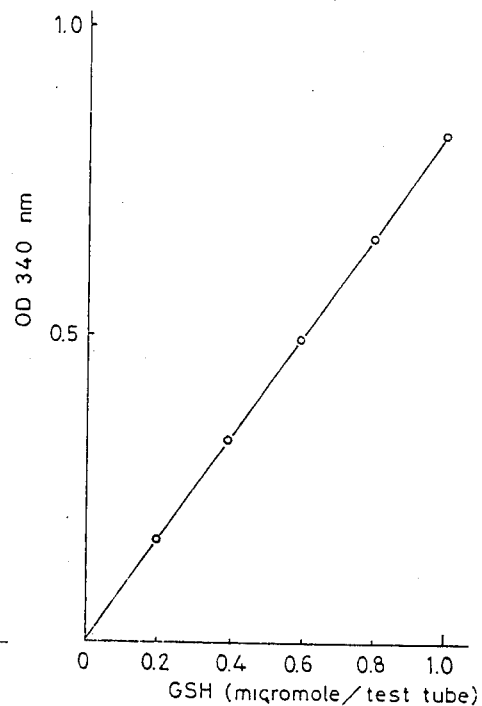

The present invention will be explained in more detail as follows by referring partly to the accompanying drawings wherein: FIG. 1 shows relationship between pH and the activity of the novel glutathione oxidase T-1 obtained by the present invention; FIG. 2 shows relationship between temperature and activity; FIG. 3 shows relationship between pH and activity after 60-minute treatment of the present enzyme at 37° C. and varying pHs; FIG. 4 shows relationship between temperature and activity after 10-minute treatment of the present enzyme at a pH of 7.0 and varying temperatures; FIG. 5 shows a visible absorption spectrum of the present enzyme (enzyme concentration, 0.45%; pH 7.0); FIG. 6 shows a calibration curve obtained in Example 3, said curve representing relationship between GSH concentration and absorbance; and FIG. 7 shows a calibration curve obtained in Example 4, said curve representing relationship between GSH concentration and absorbance.

The strain of the class Basidiomycetes used in the present invention is one belonging to the genus Calodon of the family Phylactericeae such as *Calodon suaveolens* K-1671, and one belonging to the genus Cortinarius of the family Cortinariaceae such as *Cortinarius bovinus* K-946. *Calodon suaveolens* K-1671 was isolated from the fruit body growing gregariously on the ground in coniferous forests at Mt. Fuji, and *Cortinarius bovinus* K-946 was isolated from the fruit body growing gregariously on the ground in pine forests at Mt. Kasuga in Nara Prefecture, Japan.

The formal characteristics of the fruit body and spore of the above strains are as follows:

(a) *Calodon suaveolens* K-1671

Height: about 3–5 cm.

Cap: 5–12 cm in diameter, thick, depressed and nearly round; 2 to 3 pieces of the cap join together sideways; surface is concavo-convex, has rough wrinkles and knobs, and is first nearly white and later light brown and bluish; and flesh is leathery, about 5 mm thick, soft at the upper part and tough at the lower part, and has deep blue circular pattern.

Needles: about 3–6 mm long, first dark grey and later grey brown, white at the tip and vertical to stalk.

Stalk: thick, short, hard and corky, 1–3 cm long × 0.6–1 cm thick, dark blue and has circular pattern of the same color inside.

Spores: nearly round, almost colorless and $4-6\mu \times 4-5\mu$ in size.

On comparing the above characteristics with the description in Rokuya Imazeki and Tsugio Hongo: Colored Illustrations of Fungi of Japan (published by Hoiku-sha, Co., Osaka, Japan), it is apparent that this strain is *Calodon suaveolens*. This strain is deposited at Fermentation Research Institute, Agency of Industrial Science and Technology, Japan under FERM BP-398.

(b) *Corinarius bovinus* K-946

Cap: 4–7 cm in diameter and nearly flat in an open state; surface is non-viscous, dull brown or cinnamon brown, and first white and fibrous at the circumference; gills are rough a little, adnexed to stalk, and first grey brown and later cinnamon brown.

Stalk: 5–8 cm high, as thick as 1.5–3.5 cm in diameter at the root, surrounded near the center by early falling white brim-like ring, and white above the ring and has the same color as the cap below the ring.

Spores: $7.5-10.5\mu \times 5-6.5\mu$ in size.

On comparing the above characteristics with the description in Rokuya Imazeki and Tsugio Hongo: Colored Illustrations of Fungi of Japan (published by Hoiku-sha Co., Osaka, Japan), it is apparent that this strain is *Cortinarius bovinus*. This strain is deposited at Fermentation Research Institute, Agency of Industrial Science and Technology, Japan under FERM BP-399.

Referring now to the present invention in more detail, any well-known nutrient source may be added to the culture medium, if it can be utilized by the strain used. As the carbon source, for example glycerol, glucose, starch, sucrose, maltose, lactose, dextrin, oils and fats and the like may be used. As the nitrogen source, yeast extract, peptone, defatted soybean, corn steep liquor, meat extract and the like are suitable. Also, inorganic substances and metallic salts such as phosphates, potassium salts, magnesium salts and the like may also be added. Further, vitamins and growth promoting factors may be added.

In the cultivation of the strain belonging to the class Basidiomycetes, the output of the novel glutathione oxidase T-1 varies largely depending upon the culture condition. Generally, however, the culture temperature is preferably 20° to 35° C., the pH of the culture medium is preferably 4 to 8, and the production of the novel glutathione oxidase T-1 reaches maximum by aeration/stirring culture for 3 to 15 days. In this case, it is natural that the culture condition should be determined so as to obtain a maximum output of the novel glutathione oxidase T-1 according to strains and compositions of culture medium employed. The novel glutathione oxidase T-1 produced by the strain of the present invention is present in the cultured broth, and it may be separated as precipitate by adding 20 to 90 w/v% of a soluble salt (e.g. ammonium sulfate, sodium chloride) or 50 to 80 v/v% of a hydrophilic organic solvent (e.g. ethanol, acetone) to the filtrate of the cultured broth. The precipitate obtained is desalted by dialysis or Sephadex treatment to obtain a crude enzyme solution. For purifying the crude enzyme solution obtained, the solution is adsorbed to a column of SP-Sephadex C-50 previously buffered with 0.01M acetate buffer (pH, 5.0), and the adsorbed matter is washed with 0.03M acetate buffer (pH, 5.0) and eluted with 0.01M acetate buffer (pH, 5.0) to collect the active fraction. This active fraction is then concentrated with a collodion membrane and gel-filtered through a column of Sephacryl S-200 previously buffered with 0.1M phosphate buffer (pH, 7.0) to obtain the active fraction. This active fraction is again concentrated with a collodion membrane and gel-filtered through a column of Sepharose CL-6B previously buffered with 0.1M phosphate buffer (pH, 7.0) to obtain the active fraction. This active fraction is dialyzed against water and lyophilized to obtain a purified enzyme powder. This enzyme powder is a simple substance on analyzing by polyacrylamide gel disc electrophoresis.

The enzymological and physicochemical properties of the novel glutathione oxidase T-1 of the present invention are as follows:

(1) Action:

The present enzyme, as shown by the reaction equation below, produces 1 mole of oxidized glutathione (hereinafter referred to as GSSG) and 1 mole of hydrogen peroxide from 2 moles of GSH and 1 mole of oxygen in the presence of oxygen.

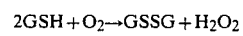

$$2GSH + O_2 \rightarrow GSSG + H_2O_2$$

(2) Substrate specificity:

The present enzyme acts on GSH alone, not on their sulfhydryl compounds at all such as L-cysteine, N-acetyl-L-cysteine L-cysteine methyl ester, cysteiamine, 2-mercaptoethanol, dithiothreitol, thiophenol, thiomalic acid, thiosalicylic acid, methylmercaptan, D-cysteine, DL-homocysteine, coenzyme A, 2-mercaptobenzimidazole, 6-mercaptopurine, etc. (measured at pHs of 5.0, 7.0 and 9.0).

(3) Optimum pH and pH stability:

The present enzyme has an optimum pH in the vicinity of 7.0 as expressed by the curve in FIG. 1.

FIG. 3 shows the pH stability of the present enzyme when the enzyme was treated at 37° C. for 60 minutes at varying pHs. As apparent from FIG. 3, the present enzyme is stable between pH 4.0 and pH 8.0. In FIGS. 1 and 3, the buffer solution used was a glycine-hydrochloride buffer for pH 3, acetate buffer for pH 4 to 5, phosphate buffer for pH 6 to 8 and borate buffer for pH 9 to 10.

(4) Optimum temperature and thermal stability:

The present enzyme has an optimum temperature in the vicinity of 50° C. as expressed by the curve in FIG. 2. FIG. 4 shows the thermal stability of the present enzyme when the enzyme was treated at a pH of 7.0 for 10 minutes at varying temperatures. The present enzyme was stable up to 60° C.

(5) Molecular weight:

The molecular weight of the present enzyme is about 450,000 by the gel filtration method with Sepharose CL-6B (produced by Pharmacia C.), and about 55,000 by SDS-polyacrylamide gel electrophoresis, which means that the present enzyme is composed of eight sub-units.

(6) Homogeneity:

Disc electrophoresis was carried out using 7.5% polyacrylamide gel (pH, 9.4) to conduct protein staining. One colored band of protein was noticed, which means that the present enzyme is a simple substance. A simple band was also noticed by SDS-polyacrylamide gel electrophoresis.

(7) Coenzyme:

The present enzyme was treated thermally or with trichloroacetic acid (TCA) and centrifuged to obtain a supernatant liquid. On subjecting this liquid to thin layer chromatography, the $R_f$ value was found to be the same as that of the standard flavine adenine dinucleotide (FAD). It was also found that this supernatant liquid is the activated substance of the apoenzyme of D-amino acid oxidase, and that FAD is the coenzyme of the present enzyme. Judging from the molecular extinction coefficient of FAD at 450 nm, 4 molecules of FAD is contained in 1 molecule of the present enzyme.

(8) Isoelectric point:

The isoelectric point of the present enzyme is 5.65±0.05 by the isoelectric focusing method with Pharmalyte (pH, 3–10; produced by Pharmacia Co.).

(9) Effect of interfering agents, metal ions and chelating agents:

The present enzyme is inhibited by PCMB (p-chloromercuribenzoic acid), sodium L-ascorbate, $Hg^{+2}$ and the like (Table 1).

TABLE 1

| Additive (1 mM) | Relative activity (%) |
|---|---|
| No addition | 100 |
| Sodium L-ascorbate | 75 |

TABLE 1-continued

| Additive (1 mM) | Relative activity (%) |
|---|---|
| L-cysteine | 100 |
| Dithiothreitol | 100 |
| 2-Mercaptoethanol | 100 |
| Thiourea | 95 |
| Potassium cyanide | 88 |
| Sodium azide | 93 |
| PCMB | 63 |
| N—ethylmaleimide | 90 |
| PMSF* | 83 |
| α,α'-Dipyridyl | 105 |
| o-Phenanthroline | 105 |
| EDTA | 90 |
| $FeCl_2$ | 100 |
| $BaCl_2$ | 107 |
| $CoCl_2$ | 90 |
| $ZnCl_2$ | 77 |
| $Pb(NO_3)_2$ | 100 |
| $HgCl_2$ | 8 |

*Phenylmethylsulfonyl fluoride

(10) Sugar content:

The present enzyme is a glycoprotein containing sugar. Its sugar content is about 40% by the phenol-sulfuric acid method.

(11) Determination of enzymatic activity:

The activity of the novel glutathione oxidase T-1 was obtained by the oxygen electrode method and by measuring the decrement of GSH. That is, reaction was carried out at 37° C. for 10 minutes using 0.1 ml of 10 mM GSH, 1.0 ml of 0.3M phosphate buffer (pH, 7.0), 1.8 ml of water and 0.1 ml of a properly diluted enzyme solution, the total volume being 3.0 ml, and an oxygen consumption rate was measured by the oxygen electrode method. The amount of enzyme consuming 1 micromole of oxygen per minute was taken as 1 unit. The decrement of GSH was measured by the George L. Ellman's method [Arch. Biochem. and Biophys., Vol. 82, pp. 70 (1959)], and the amount of enzyme decreasing 2 micromoles of GSH per minute was taken as 1 unit.

Comparison of the novel glutathione oxidase T-1 of the present invention with the conventional sulfhydryl oxidase or glutathione sulfhydryl oxidase is shown in Table 2.

TABLE 2

| | Novel glutathione oxidase T-1 | Sulfhydryl oxidase isolated from rat seminal vesicle secretion*1 | Glutathione sulfhydryl oxidase*2 |
|---|---|---|---|
| Action | $2GSH + O_2 \rightarrow GSSG + H_2O_2$ | $2RSH + O_2 \rightarrow RSSR + H_2O_2$ | $2GSH + O_2 \rightarrow GSSG + H_2O_2$ |
| Substrate specificity | Acts on GSH alone. | Relative activity (at pH 7.4):<br>　GSH　100%<br>　L-cysteine　56%<br>　Dithiothreitol　32%<br>and acts also on other SH compounds. | Acts on GSH, L-cysteine, 2-mercaptoethanol, dithiothreitol, etc. |
| Stability | Stable up to 60° C. for 10-minute treatment at pH 7.0. Stable in the pH range of 4 to 8 for 60-minute treatment at 37° C. | 50% remains for 3.5-minute treatment at 60° C. | Stable up to 55° C. for 15-minute treatment at pH 7.4. Stable in the pH range of 5 to 9 for 15-minute treatment at 45° C. |
| Optimum temperature | 50° C. | | 30° to 50° C. |
| Optimum pH | 7.0 | 7.0 | 7.1 to 7.8 |
| Molecular weight | About 450000 (gel filtration method). About 55000 (SDS-polyacrylamide gel electrophoresis). | About 66000 | About 94000 (gel filtration method) About 47000 (SDS-polyacrylamide gel electrophoresis). |
| Isoelectric point | 5.65 ± 0.05 | 7.45 | 4.21 |
| Interfering agent | $Hg^{+2}$, p-chloromercuribenzoic acid | | $Zn^{2+}$ |
| Coenzyme | FAD | FAD | FAD |

TABLE 2-continued

| Novel glutathione oxidase T-1 | Sulfhydryl oxidase isolated from rat seminal vesicle secretion*1 | Glutathione sulfhydryl oxidase*2 |
|---|---|---|
| Sugar content About 40% | | |

In the above table:
*1 Enzyme described in Biochemistry, Vol. 19, pp 2639 (1980).
*2 Enzyme described in Japanese Patent Application Kakai (Laid-open) No. 132879/1982.

The reagent composition containing the novel glutathione oxidase T-1 of the present invention may contain the common components other than said novel glutathione oxidase T-1. The amount of enzyme contained in the reagent composition is at least not less than 0.001 unit, preferably 10 to 0.01 units, and it is properly regulated according to the measurement time and uses. In addition, the well-known buffer solutions, stabilizers for enzyme, etc. may be added if necessary. The reagent composition is provided by the well-known methods such as dissolution, lyophilization, impregnation into carrier sheet and the like. Also, the enzyme may be used in an insoluble carrier-bound form prepared according to the well-known methods.

Quantitative determination of GSH

According to the present invention, the GSH content of biological fluids (e.g. blood serum, urine) and foods can be determined quantitatively by utilizing the foregoing property [(1) Action described above] of the novel glutathione oxidase T-1. Since the novel glutathione oxidase T-1 of the present invention produces 1 mole of GSSG and 1 mole of hydrogen peroxide from 2 moles of GSH and 1 mole of oxygen in the presence of oxygen, the quantitative determination of GSH in biological fluids and foods can easily be attained by causing the novel glutathione oxidase T-1 to act on GSH and measuring the amount of the formed hydrogen peroxide or consumed oxygen. The measurement method for hydrogen peroxide is roughly divided into spectroscopic methods, fluorescence methods and electrochemical methods, of which the spectroscopic method using the aforementioned hydrogen peroxide-peroxidase-hydrogen-donative chromogen reaction is most popularly used. In this case, since GSH, which is the substrate of the present enzyme, interferes with the foregoing color-development reaction, it is preferred to treat as follows: The novel glutathione oxidase T-1 is thoroughly caused to act on test samples such as GSH-containing biological fluids or foods, an SH-group sequestering agent (e.g. N-ethylmaleimide) is added so that other SH compounds present in the test sample do not interfere with the peroxidase-hydrogen donor color-development reaction, and then the system is led to the peroxidase-hydrogen donor color-development system. The reaction between the novel glutathione oxidase T-1 and the test sample may be carried out under suitable conditions according to the components to be determined present in biological fluids or foods, determination methods employed and the like. Generally, however, the following procedure is employed: 0.05 to 1 unit of the novel glutathione oxidase T-1 and a buffer solution (pH, 6 to 8) are added to 10 to 100 μl of the test sample (e.g. biological fluids, foods); after carrying out reaction at 20° to 50° C., preferably 37° C. for 1 to 30 minutes, preferably 5 to 10 minutes, N-ethylmaleimide is added so that its final concentration is 1 to 10 micromoles/ml; after standing for 5 to 10 minutes at room temperature, the peroxidase-hydrogen-donative chromogen, e.g. 4-aminoantipyrine and phenol, is added, and the formed red quinone dye is measured at 500 nm to obtain the GSH content of the test sample. Other spectroscopic methods for the determination of hydrogen peroxide include for example a method in which formaldehyde is produced from hydrogen peroxide in the presence of methanol and catalase; the formaldehyde is reacted with nicotinamide adenine dinucleotide (hereinafter referred to as NAD) in the presence of formaldehyde dehydrogenase to produce reduced nicotinamide adenine dinucleotide (hereinafter referred to as NADH); and then the GSH content of the test sample is determined based on an increase in the absorbance at 340 nm due to NADH. Generally, this method is carried out as follows: Excess amounts of methanol and catalase are added to 10 to 100 μl of the test sample (e.g. biological fluids, foods), and then NAD and formaldehyde dehydrogenase are added so that their final concentrations are 0.1 to 1.0 micromole/ml and 0.2 to 1.0 unit/ml, respectively; to the resulting solution are added 0.05 to 0.5 unit of the novel glutathione oxidase T-1 and a buffer solution (pH, 7 to 8), and reaction is carried out at 25° to 50° C., preferably 37° C. for 1 to 30 minutes, preferably 5 to 10 minutes to produce NADH; and then the GSH content of the test sample is determined based on an increase in the absorbance at 340 nm due to NADH. Also, for measurement of the amount of consumed oxygen, Warburg's pressure-detection method and the oxygen electrode method are well known [Biochemical Experiment Course: Vol. 5 Enzyme Research Technique (No. 1), pp. 35–52, published by Tokyo Kagaku-dojin Co., Japan, 1975]. Also, an oxygen electrode method in which the detection part of the oxygen electrode has immobilized novel glutathione oxidase T-1, may be employed.

GSH effect-eliminating method in the analysis of components of biological fluids or foods In analyzing various components in biological fluids (e.g. blood serum, urine) or foods by utilizing the oxidase-peroxidase-hydrogen-donative chromogen reaction, a method for removing the coexisting GSH with the novel glutathione oxidase T-1 will be explained. As described in the foregoing property [(1) Action described above], the present enzyme produces hydrogen peroxide indicating the oxidase-peroxidase-hydrogen-donative chromogen reaction. Consequently, in order to use the present enzyme in analyzing various components in biological fluids and foods, it is necessary to decompose hydrogen peroxide, as formed by the enzyme reaction, in advance with catalase, add an interfering agent for catalase, e.g. sodium azide, to the reaction solution to completely inhibit the action of catalase and then to lead the system to one in which measurement of various components is carried out. Also in this case, the reaction between the novel glutathione oxidase T-1 and the test sample may be carried out under suitable conditions according to the components to be determined present in biological fluids or foods and determination methods employed. Generally, 0.05 to 1 unit of the novel glutathione oxidase T-1, 50 to 200 units of catalase and a buffer solution (pH, 6 to 8) are added to 10 to 100 μl of the test sample (e.g. biological fluids, foods), and after carrying out reaction at 20° to 50° C., preferably 37° C. for 1 to 30 minutes, preferably 5 to 10 minutes, sodium azide is added so that its final concentration is 1 to 10 micromoles/ml. The subsequent treatment may be carried out according to the common measurement method for each component using peroxidase and a hydrogen-donative chromogen. Also, in the treatment method described above, such a method may be employed that sodium azide is previously added to a reagent for measurement of each component, and then the resulting mixture is added to the test sample treated with the novel glutathione oxidase T-1.

Next, the present invention will be illustrated with reference to the following examples, but it is not to be interpreted as being limited to these examples.

EXAMPLE 1

Production of novel glutathione oxidase T-1

A slant culture medium comprising 2% of glucose, 0.5% of Ebios and 1.5% of agar (Ebios medium) was inoculated with *Calodon suaveolens* K-1671, and cultivation was carried out by keeping the medium still at 25° C. for one week to obtain a seed fungus. Separately from this, 100 ml of a culture medium comprising 2.0% of glucose, 0.3% of yeast extract, 1% of peptone, 0.3% of $KH_2PO_4$ and 0.1% of $MgSO_4.7H_2O$ was added to a 500-ml Erlenmeyer flask, and after sterilized at 120° C. for 20 minutes, it was cooled and inoculated with the above seed fungus. Thereafter, cultivation was carried out at 25° C. for 4 days to prepare a seed cultured broth. Separately from this, 20 liters of a culture medium comprising 2% of glucose, 0.1% of yeast extract, 2% of peptone, 0.3% of $KH_2PO_4$, 0.1% of $MgSO_4.7H_2O$ and 0.02% (v/v) of a defoaming agent (CB-442; produced by Nippon Yushi Co.) was added to a 30-liter jar fermenter, and sterilized at 120° C. for 20 minutes. After cooling, the culture medium was inoculated with 100 ml of the above seed cultured broth, and cultivation was carried out at 27° C. for 3 days under the condition that the aeration rate was 20 liters per minute and the stirring rate was 250 revolutions per minute. After completion of the cultivation, the mycelium was removed by filtration to obtain a culture filtrate. The novel glutathione oxidase T-1 activity of this culture filtrate was 0.42 unit/ml. After concentrating 16 liters of this culture filtrate on a ultrafilter membrane having a molecular weight of 15000, ammonium sulfate was added until 90% saturation. After allowing to stand for a whole day and night, the resulting ammonium sulfate precipitate was dialyzed for a whole day and night against a large quantity of 0.01M acetate buffer (pH, 5.0). The crude enzyme solution thus obtained was adsorbed to a column (φ5.0 cm × 20 cm) of SP-Sephadex C-50 previously buffered with 0.01M acetate buffer (pH, 5.0), and the adsorbed matter was washed with 0.03M acetate buffer (pH, 5.0) and eluted with a 0.1M acetate buffer (pH, 5.0). The active fraction, an eluate, was concentrated on a collodion membrane and gel-filtered through a column (φ3.6 × 90 cm) of Sephacryl S-200 previously buffered with 0.1M phosphate buffer (pH, 7.0). This active fraction was again concentrated on a collodion membrane and gel-filtered through a column (φ2.5 cm × 105 cm) of Sepharose CL-6B previously buffered with 0.1M phosphate buffer (pH, 7.0). The active fraction thus obtained was dialyzed against water and lyophilized to obtain 20 mg of a purified enzyme powder. The specific activity of this powder was 90 units/mg. This enzyme powder was a simple substance on analyzing by polyacrylamide gel disc electrophoresis. The purification step described above is shown in Table 3.

TABLE 3

| | Total protein content (mg) | Total activity (U) | Specific activity (U/mg) | Yield (%) |
|---|---|---|---|---|
| Culture filtrate | 67100 | 6680 | 0.100 | 100 |
| Ultra-filtration | 30700 | 6500 | 0.212 | 97.3 |
| Salting-out with ammonium sulfate | 6600 | 4740 | 0.718 | 71.0 |
| SP-Sephadex C-50 | 84 | 2230 | 26.5 | 33.4 |
| Sephacryl S-200 | 21.2 | 1885 | 88.8 | 28.2 |
| Sepharose CL-6B | 20.0 | 1800 | 90.0 | 26.9 |

EXAMPLE 2

Production of novel glutathione oxidase T-1

The Ebios culture medium of Example 1 was inoculated with *Cortinarius bovinus* K-946, and cultivation was carried out by keeping the medium still at 25° C. for one week to obtain a seed fungus. Separately from this, 100 ml of a culture medium comprising 2.0% of glucose, 0.3% of yeast extract, 1% of peptone, 0.3% of $KH_2PO_4$ and 0.1% of $MgSO_4.7H_2O$ was added to a 500-ml Erlenmeyer flask, and after sterilized at 120° C. for 20 minutes, it was inoculated with the above seed fungus. Shake culture was then carried out at 25° C. for 7 days. The novel glutathione oxidase T-1 activity of the culture filtrate obtained was 0.15 unit/ml.

EXAMPLE 3

Quantitative determination of GSH (1) Color-developing reagent:

167 mg of 4-aminoantipyrine, 1.32 g of phenol and 80 mg (100 units/mg) of peroxidase from Horseradish (type I; produced by Sigma Chemical Co., U.S.A. ) were dissolved in 100 ml of a 0.1M potassium phosphate buffer (pH, 7.0).

(2) Novel glutathione oxidase T-1 solution:

5 mg (90 units/mg) of the purified enzyme was dissolved in 100 ml of 0.1M potassium phosphate buffer (pH, 7.0) (4.5 units/ml).

(3) N-ethylmaleimide solution:

500 mg of N-ethylmaleimide was dissolved in 100 ml of 0.1M potassium phosphate buffer (pH, 7.0) (40 micromoles/ml).

(4) Procedure:

To a test tube were added 0.1 ml of the novel glutathione oxidase T-1 solution, 1 ml of 0.2M potassium phosphate buffer (pH, 7.0) and 1.4 ml of distilled water, and the tube was placed in a constant-temperature incubator (37° C.). To this solution was added 0.1 ml of a standard GSH solution (2 to 20 micromoles/ml), and reaction was carried out for 10 minutes with shaking. Thereafter, 0.1 ml of the N-ethylmaleimide solution was added, and after standing at room temperature for 5 minutes, 0.3 ml of the color-developing reagent was added. The absorbance at 500 nm of the solution was measured with a blank solution containing no novel glutathione oxidase T-1 as a control to prepare a calibration curve (FIG. 6).

As shown in FIG. 6, the absorbance at 500 nm increases in proportion to the amount of GSH, and from this, the GSH content of biological fluids (e.g. blood serum, urine) or foods can accurately be determined.

EXAMPLE 4

Quantitative determination of GSH (1) Catalase solution:

10 mg of catalase from bovine liver [3000 units/mg; produced by P.L. Biochemical Co., U.S.A.] was dissolved in 3 ml of 0.1M potassium phosphate buffer (pH, 7.5).

(2) NAD solution:

441.3 mg of NAD was dissolved in 10 ml of distilled water.

(3) Formaldehyde dehydrogenase solution:

22 mg of formaldehyde dehydrogenase [1.8 units/mg; produced by TOYOBO Co.] was dissolved in 2 ml of 0.1M potassium phosphate buffer (pH, 7.5).

(4) Novel glutathione oxidase T-1 solution:

2 mg (90 units/mg) of the purified enzyme was dissolved in 100 ml of 0.1M potassium phosphate buffer (pH, 7.5) (1.8 units/ml).

(5) Procedure:

To a test tube were added 0.1 ml of the novel glutathione oxidase T-1 solution, 1 ml of 0.3M potassium phosphate buffer (pH, 7.5), 0.1 ml of 2.4% (v/v) Triton X-100 solution, 0.1 ml of the catalase solution, 0.1 ml of the NAD solution, 0.1 ml of the formaldehyde dehydrogenase solution, 0.9 ml of distilled water and 0.5 ml of methanol (2 moles/liter), and the tube was placed in a constant-temperature incubator (37° C.). To this solution was added 0.1 ml of a standard GSH solution (1 to 10 micromoles/ml), and reaction was carried out for 10 minutes with shaking. Thereafter, the absorbance at 340 nm due to NADH of the solution was measured with a blank solution containing no novel glutathione oxidase T-1 as a control to prepare a calibration curve (FIG. 7).

As shown in FIG. 7, the absorbance at 340 nm is observed to increase in proportion to the amount of GSH, and from this, the GSH content of test samples can be determined.

EXAMPLE 5

Elimination of the interference of GSH in a determination system for total cholesterol in blood serum (1) Novel glutathione oxidase T-1 solution:

The enzyme solution of Example 4 was used.

(2) Catalase solution:

5 mg of catalase from bovine liver [3000 units/mg; produced by P.L. Biochemical Co., U.S.A.] was dissolved in 10 ml of 0.1M potassium phosphate buffer (pH, 7.0).

(3) Sodium azide solution:

26 mg of sodium azide was dissolved in 10 ml of distilled water.

(4) Color-developing reagent:

The color-developing reagent of Example 3 was used.

(5) Cholesterol esterase solution:

5 mg of the purified cholesterol esterase authentic sample (70 units/mg; produced by TAKARA SHUZO Co.) was dissolved in 10 ml of 0.1M potassium phosphate buffer (pH, 7.0) (35 units/ml).

(6) Cholesterol oxidase solution:

10 mg of the purified cholesterol oxidase authentic sample (15 units/mg; produced by TAKARA SHUZO Co.) was dissolved in 5 ml of 0.1M potassium phosphate buffer (pH, 7.0) (30 units/ml).

(7) Procedure:

To a test tube were added 0.1 ml of the novel glutathione oxidase T-1 solution, 1 ml of 0.3M potassium phosphate buffer (pH, 7.0), 0.3 ml of 3% Triton X-100 solution, 0.1 ml of Control Serum (produced by Hyland Co., U.S.A.) and 0.1 ml of the catalase solution, and the test tube was placed in a constant-temperature incubator (37° C.). To this solution was added 0.1 ml of a standard GSH solution (1 to 6 micromoles/ml), and reaction was carried out for 5 minutes with stirring. Thereafter, 0.1 ml of the sodium azide solution, 0.3 ml of the color-developing reagent, 0.1 ml of the cholesterol esterase solution, 0.1 ml of the cholesterol oxidase solution and 0.7 ml of distilled water were added, and after carrying out reaction for 10 minutes, the absorbance at 500 nm was measured. Separately, the absorbance of a solution containing no novel glutathione oxidase T-1 was measured as a control. By the means as described above, the effect of the present enzyme to eliminate the color-development interference of GSH in a determination system for total cholesterol in blood serum was examined. The results are shown in Table 4.

TABLE 4

| Method | OD 500 nm Amount of GSH (micromole) | | | | |
| --- | --- | --- | --- | --- | --- |
| | 0 | 0.1 | 0.2 | 0.4 | 0.6 |
| Present method | 0.667 | 0.655 | 0.665 | 0.652 | 0.653 |
| No addition of novel glutathione oxidase T-1 | 0.660 | 0.552 | 0.505 | 0.420 | 0.378 |

As apparent from Table 4, by using the method of the present invention, it became possible to eliminate the interference of GSH to obtain an accurate value of total cholesterol in blood serum.

EXAMPLE 6

Elimination of the interference of GSH in a determination system for glucose in blood serum.

(1) Novel glutathione oxidase T-1 solution:

The enzyme solution of Example 4 was used.

(2) Catalase solution:

The catalase solution of Example 5 was used.

(3) Sodium azide solution:

The sodium azide solution of Example 5 was used.

(4) Color-developing reagent:

The color-developing reagent of Example 3 was used.

(5) Glucose oxidase solution:

20 mg of glucose oxidase (100 units/mg; produced by TOYOBO Co.) was dissolved in 2 ml of 0.1M potassium phosphate buffer (pH, 7.0) (1000 units/ml).

(6) Procedure:

To a test tube were added 0.1 ml of the novel glutathione oxidase T-1 solution, 1 ml of 0.3M potassium phosphate buffer (pH, 7.0), 0.1 ml of Control Serum (produced by Hyland Co., U.S.A.) and 0.1 ml of the catalase solution, and the tube was placed in a constant-temperature incubator (37° C.). To this solution was added 0.1 ml of a standard GSH solution (1 to 10 micromoles/ml), and reaction was carried out for 5 minutes with shaking. Thereafter, 0.1 ml of the sodium azide solution, 0.3 ml of the color-developing reagent, 0.1 ml of the glucose oxidase solution and 1.1 ml of distilled water were added, and after carrying out reaction for 10 minutes, the absorbance at 500 nm was measured. Separately, the absorbance of a solution containing no novel glutathione oxidase T-1 was measured as a control. By the means as described above, the effect of the present enzyme to eliminate the color-development interference of GSH in a determination system for glucose in a blood serum was examined. The results are shown in Table 5.

TABLE 5

| Method | OD 500 nm Amount of GSH (micromole) | | | | | | |
| --- | --- | --- | --- | --- | --- | --- | --- |
|  | 0 | 0.1 | 0.2 | 0.4 | 0.6 | 0.8 | 1.0 |
| Present method | 0.900 | 0.912 | 0.910 | 0.895 | 0.898 | 0.905 | 0.902 |
| No addition of novel glutathione oxidase T-1 | 0.905 | 0.872 | 0.795 | 0.680 | 0.638 | 0.522 | 0.470 |

As apparent from Table 5, by using the method of the present invention, it became possible to eliminate the interference of GSH to obtain an accurate value of glucose in blood serum.

What is claimed is:

1. A novel glutathione oxidase T-1 having the following physicochemical properties:
   (1) Action: Acts on reduced glutathione in the presence of oxygen to produce oxidized glutathione and hydrogen peroxide;
   (2) Substrate specificity: Acts on reduced glutathione alone, not on other sulfhydryl compounds at all;
   (3) Optimum pH and pH stability: Has an optimum pH in the vicinity of 7.0, and is stable between pH 4.0 and pH 8.0 for 60-minute treatment at 37° C.;
   (4) Optimum temperature and thermal stability: Has an optimum temperature in the vicinity of 50° C., and is stable up to 60° C. for 10-minute treatment at a pH of 7.0;
   (5) Molecular weight: About 450000 by the gel filtration method, and about 55000 by sodium dodecyl sulfate (SDS)-polyacrylamide gel electrophoresis, from which said novel glutathione oxidase T-1 is composed of eight subunits;
   (6) Coenzyme: Contains flavine adenine dinucleotide (FAD), a coenzyme, of 4 molecules/molecule;
   (7) Isoelectric point: 5.65±0.05;
   (8) Interfering agent: $Hg^{2+}$, p-chloromercuribenzoic acid, sodium L-ascorbate, etc;
   (9) Sugar content: About 40%.

2. A reagent composition for reduced glutathione characterized in that said composition contains the novel glutathione oxidase T-1 as described in claim 1.

3. A method for the quantitative determination of reduced glutathione characterized in that reduced glutathione in test samples is oxidized with said novel glutathione oxidase T-1 in the presence of oxygen, and the reduced glutathione is quantitatively determined based on the amount of consumed oxygen or formed hydrogen peroxide in the reaction solution.

4. A method for producing said novel glutathione oxidase T-1 characterized in that a novel glutathione oxidase T-1 producing strain belonging to the genus Calodon or Cortinarius is cultured and the novel glutathione oxidase T-1 produced is collected from the cultured broth obtained.

5. A method as described in claim 4, wherein said novel glutathione oxidase T-1 producing strain belonging to the genus Calodon is *Calodon suaveolens* K-1671.

6. A method as described in claim 4, wherein said novel glutathione oxidase T-1 producing strain belonging to the genus Cortinarius is *Cortinarius bovinus* K-946.

7. A novel glutathione oxidase T-1 according to claim 1 in which it has such physiochemical properties as in (1) that it acts on reduced glutathione in the presence of oxygen but not on L-cysteine, D-cysteine, N-acetyl-L-cysteine, L-cysteine methylester, cysteamine, thiophenol, 2-mercaptoethanol and dithiothreitol.

* * * * *